United States Patent [19]
Gonzalez

[11] Patent Number: 5,307,094
[45] Date of Patent: Apr. 26, 1994

[54] SUNGLASS RAISING AND LOWERING APPARATUS

[76] Inventor: Danny Gonzalez, 107 Oxford St., San Francisco, Calif. 94134

[21] Appl. No.: 38,821

[22] Filed: Mar. 29, 1993

[51] Int. Cl.⁵ ............................ G02C 3/02; A61F 9/00
[52] U.S. Cl. .................................... 351/59; 351/155; 351/158; 2/10; 2/209.13
[58] Field of Search ........... 351/41, 44, 47, 57, 351/59, 63, 155, 158; 2/10, 12, 209.13

[56] References Cited

U.S. PATENT DOCUMENTS

| | | | |
|---|---|---|---|
| 256,393 | 4/1882 | Shone | 351/155 |
| 1,288,284 | 12/1918 | Taylor | 351/155 |
| 2,654,089 | 10/1953 | Tannenbaum | 2/10 |
| 4,152,051 | 5/1979 | Van Tiem et al. | 351/59 |
| 4,869,586 | 9/1989 | Chung | 351/155 X |
| 4,885,808 | 12/1989 | Carpenter | 351/59 X |
| 4,951,316 | 8/1990 | Moody | 351/155 X |
| 4,976,530 | 12/1990 | Mackay et al. | 351/44 |

*Primary Examiner*—William L. Sikes
*Assistant Examiner*—David R. Parsons
*Attorney, Agent, or Firm*—Leon Gilden

[57] ABSTRACT

A sun visor includes an annular band for securement of the sun visor about an individual's uppermost head portion, wherein the sun visor includes an eyeglass assembly mounted rotatably to a concave portion of the sun visor, wherein a photocell in cooperation with a battery and solenoid drive is arranged to effect rotation of the eyeglass assembly to a lowered second position from a raised first position that is in adjacency to the sun visor concave surface in response to available sunlight.

4 Claims, 4 Drawing Sheets

SUNGLASS RAISING AND LOWERING APPARATUS

BACKGROUND OF THE INVENTION

1. Field of the Invention

The field of invention relates to visor apparatus, and more particularly pertains to a new and improved sunglass raising and lowering apparatus in cooperation with a sun visor to effect raising and lowering of the sunglass assembly in response to variation in available sunlight.

2. Description of the Prior Art

Sun visor structure of various types have been employed in the prior art for affording protection to an individual's eyes during use, wherein a sun visor construction is indicated in U.S. Pat. No. 4,976,530 with the use of sunglasses typically limited relative to the independent use relative to a sun visor structure.

The instant invention attempts to overcome deficiencies of the prior art by providing for a sun visor having an eyeglass assembly pivotally mounted relative to the sun visor in response to sunlight being detected by the associated photo-cell structure and in this respect, the present invention substantially fulfills this need.

SUMMARY OF THE INVENTION

In view of the foregoing disadvantages inherent in the known types of sun visor apparatus now present in the prior art, the present invention provides a sunglass raising and lowering apparatus wherein the same is directed to the lowering of a sunglass assembly in response to a photo-cell detection of available sunlight at predetermined levels. As such, the general purpose of the present invention, which will be described subsequently in greater detail, is to provide a new and improved sunglass raising and lowering apparatus which has all the advantages of the prior art sun visor apparatus and none of the disadvantages.

To attain this, the present invention provides a sun visor including an annular band for securement of the sun visor about an individual's uppermost head portion, wherein the sun visor includes an eyeglass assembly mounted rotatably to a concave portion of the sun visor, wherein a photo-cell in cooperation with a battery and solenoid is arranged to effect rotation of the eyeglass assembly to a lowered second position from a raised first position that is in adjacency to the sun visor concave surface in response to available sunlight.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved sunglass raising and lowering apparatus which has all the advantages of the prior art sun visor apparatus and none of the disadvantages.

It is another object of the present invention to provide a new and improved sunglass raising and lowering apparatus which may be easily and efficiently manufactured and marketed.

It is a further object of the present invention to provide a new and improved sunglass raising and lowering apparatus which is of a durable and reliable construction.

An even further object of the present invention is to provide a new and improved sunglass raising and lowering apparatus which is susceptible of a low cost of manufacture with regard to both materials and labor, and which accordingly is then susceptible of low prices of sale to the consuming public, thereby making such sunglass raising and lowering apparatus economically available to the buying public.

Still yet another object of the present invention is to provide a new and improved sunglass raising and lowering apparatus which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
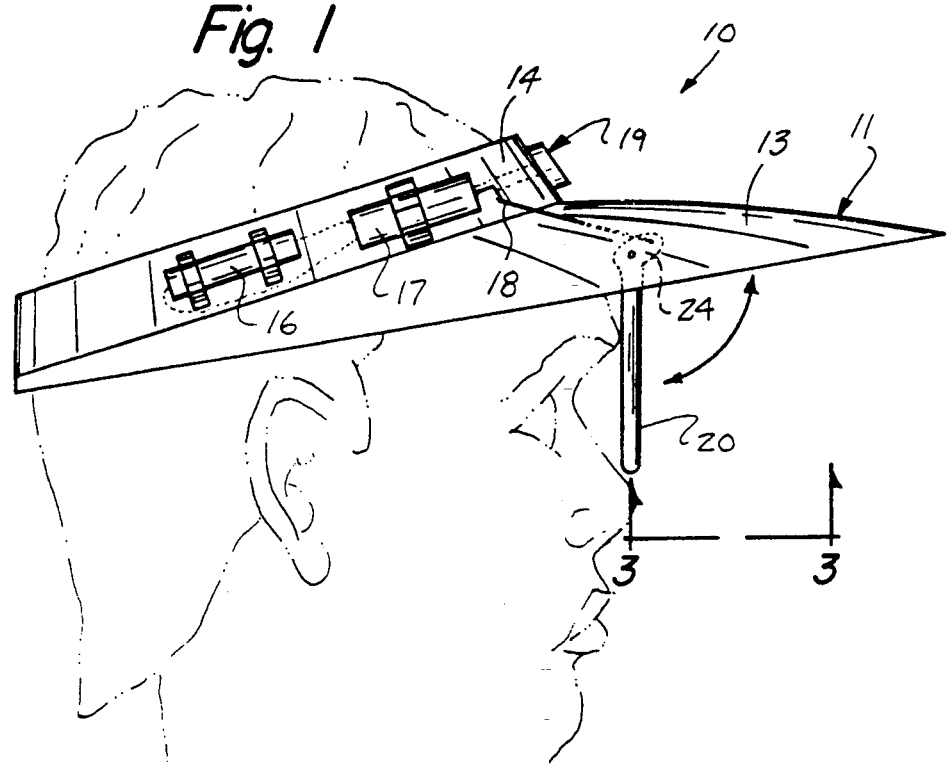
FIG. 1 is an orthographic side view of the invention.
Figure 2:
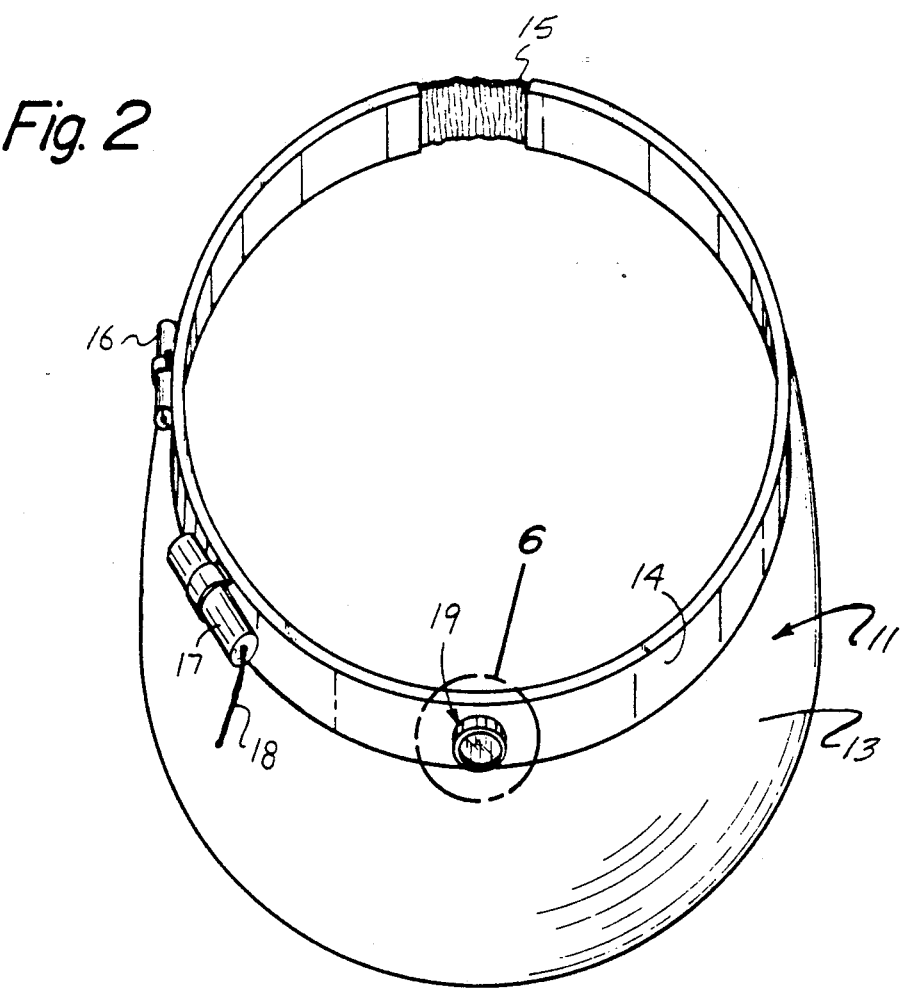
FIG. 2 is an orthographic top view of the invention
Figure 3:
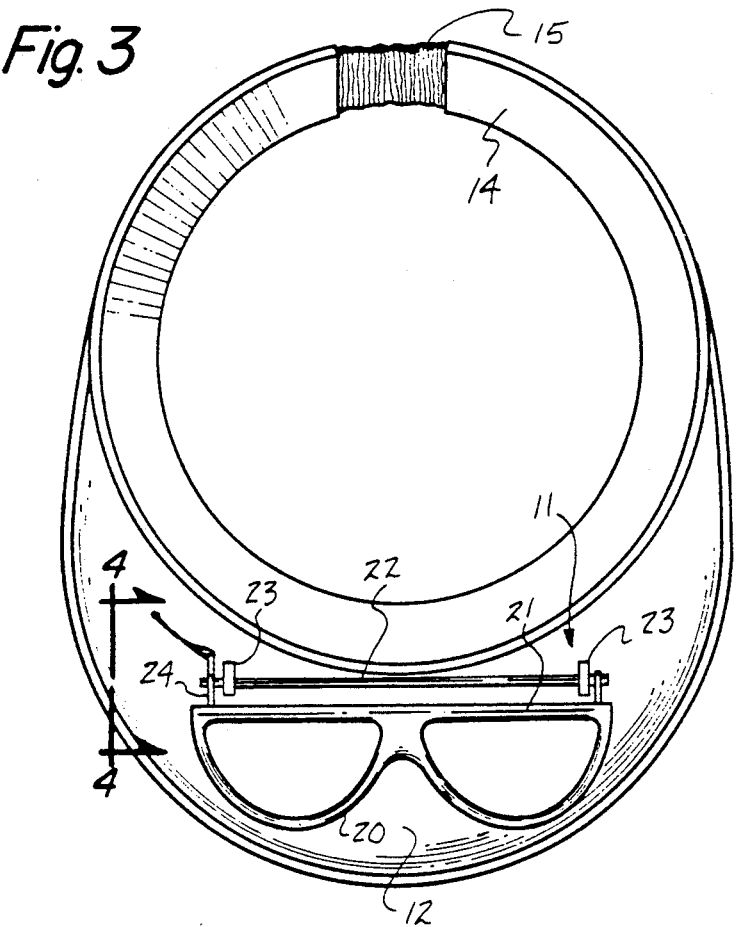
FIG. 3 is an orthographic view, taken along the lines 3—3 of FIG. 1 in the direction indicated by the arrows.

With reference now to the drawings, and in particular to FIGS. 1 to 8 thereof, a new and improved sunglass raising and lowering apparatus embodying the principles and concepts of the present invention and generally designated by the reference numeral 10 will be described.

Figure 4:
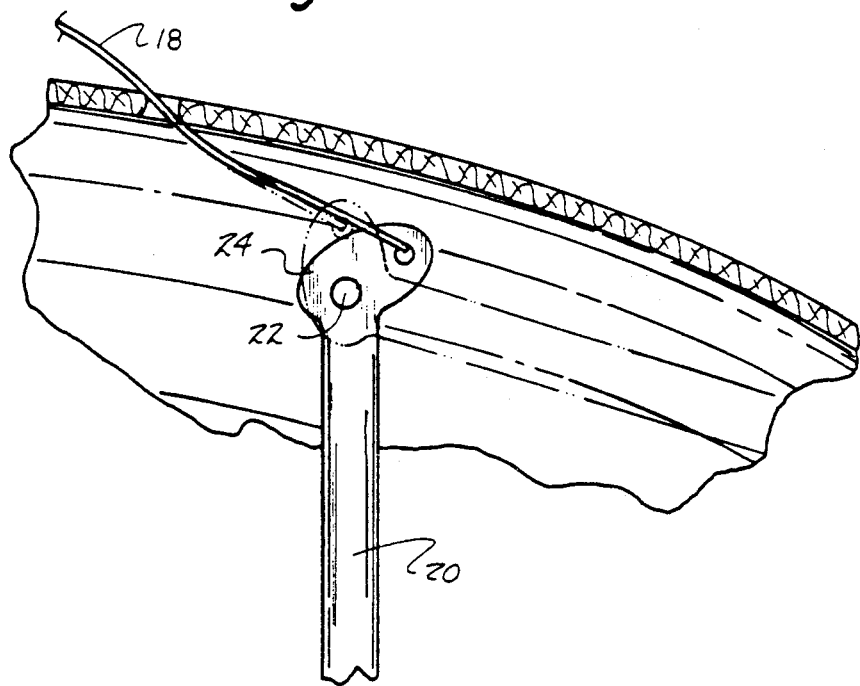
FIG. 4 is an orthographic view, taken along the lines 4—4 of FIG. 3 in the direction indicated by the arrows.

More specifically, the sunglass raising and lowering apparatus 10 of the instant invention essentially comprises a sun visor 11 having a visor concave bottom surface 12 coextensive with a visor convex top surface 13. A continuous annular band 14 is joined to the sun visor, with the band 14 having an elastomeric web portion 15 to accommodate the band relative to an individual's head portion, as indicated in FIG. 1. A battery 16 and a solenoid 27 are mounted to the band 14 in electrical communication relative to one another, and a photo-cell switch assembly 19 mounted to the band medially of and above the visor convex top surface 13. A solenoid link 18 extends from the solenoid through the visor into mechanical communication with a sunglass set 20. The sunglass set 20 includes a frame leg 21 extending over the lenses of the sunglass set 20, wherein the frame leg 21 is arranged in a parallel orientation relative to an axle shaft 22 that is mounted within a plurality of support blocks 23 to the concave bottom surface 12. The axle shaft 22 rotatably mounts a cam plate 24 that in turn is integrally secured to the frame leg 21. The solenoid link 18 in turn is eccentrically mounted to the cam plate 24 relative to the axle shaft 22, whereupon rotation of the cam plate 24 effects rotation of the sunglass set 20 from a first position, as indicated in phantom in FIG. 4, to a second position, as indicated in FIG. 4 in solid line, to indicate the operative orientation of the sunglasses relative to an individual's eyes, as indicated in FIG. 1 also.

Figure 5:
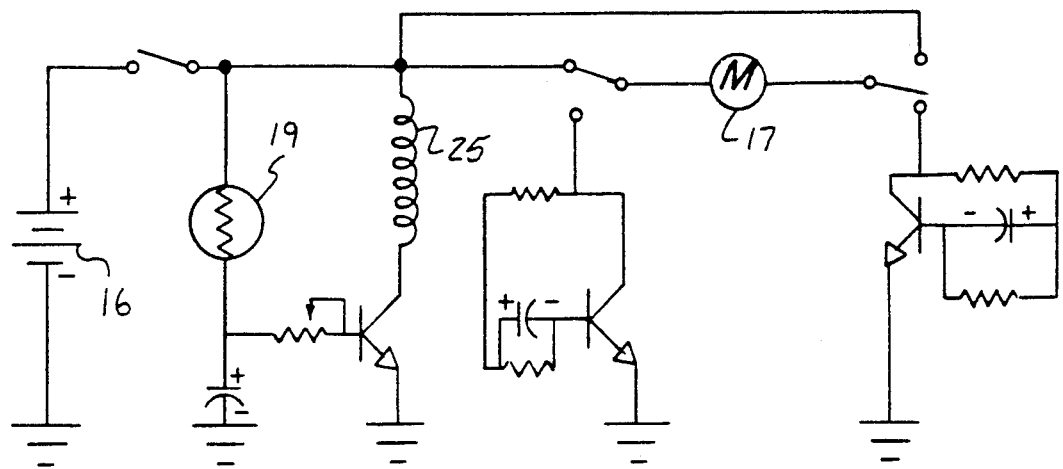
FIG. 5 is a diagrammatic illustration of a typical photo-cell circuitry for use by the invention.

The FIG. 5 indicates a typical photo-cell relay, having a relay coil 25 cooperative with the photo-cell 19 and the battery 16 to operate the solenoid 17, utilizing the transistor and capacitor structure through the switching arrangement, as indicated. A variation in electrical communication between the photo-cell and the solenoid is available to one of ordinary skill in the art and the circuitry provided is by way of example and is not intended to limit the intercommunication of the photo-cell 19 relative to actuation of the solenoid 17 to effect pivoting of the sunglass set 20, as indicated by arrow in FIG. 1 for example.

Figure 6:
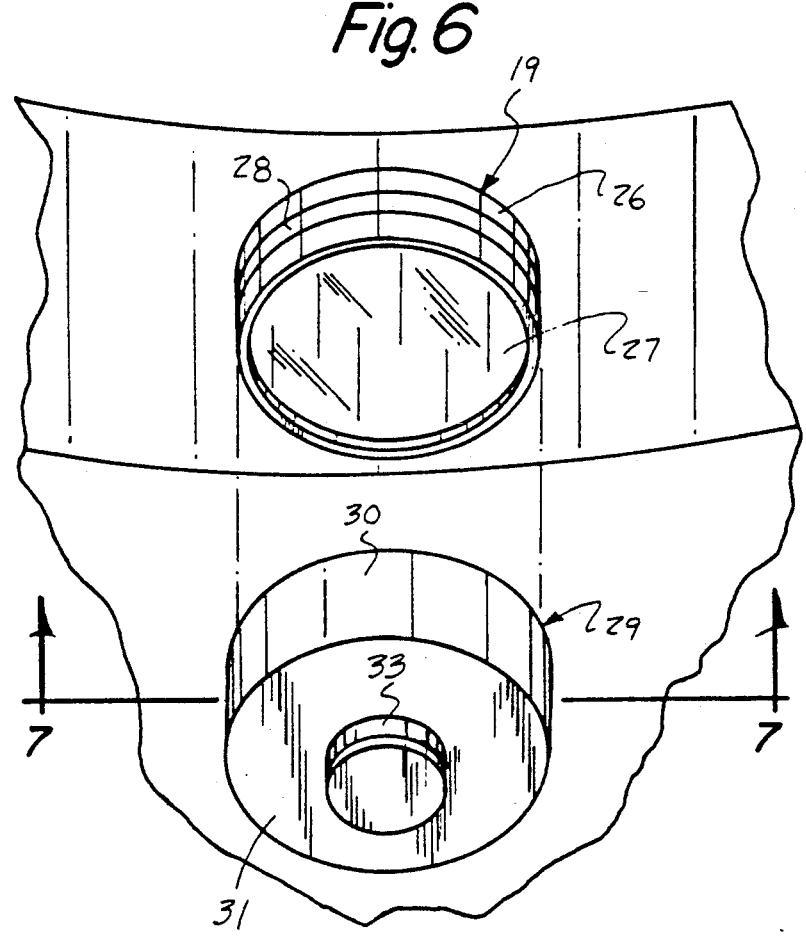
FIG. 6 is an enlarged isometric illustration of the photo-cell lens in cooperation with an illumination cap.

The FIG. 6 indicates the use of the photo-cell having a cylindrical housing 26 mounting a photo-cell plate 27 therewith. A ferrous metallic ring 28 is arranged in surrounding relationship relative to the cylindrical housing 26 for cooperation with a cap member 29. The cap member 29 is arranged for use by individuals when it is desired to maintain orientation of the sunglass set in the second position, as indicated in FIG. 1.

Figure 7:
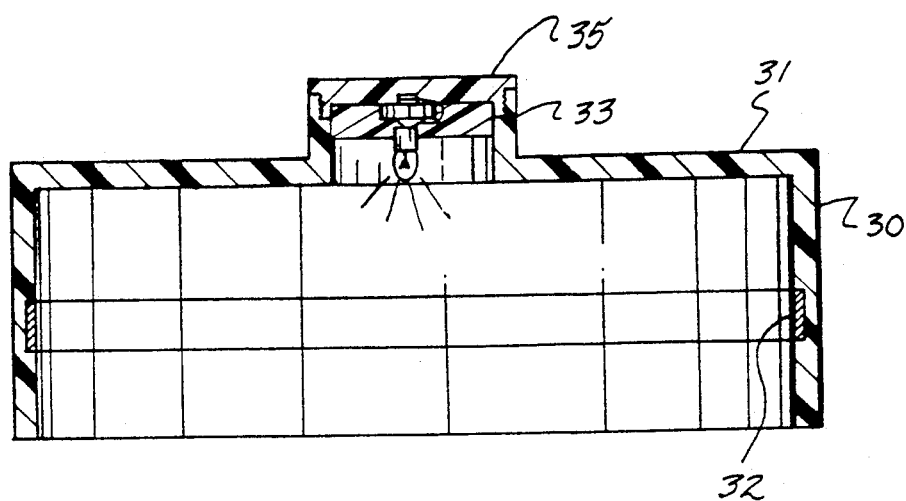
FIG. 7 is an orthographic view, taken along the lines 7—7 of FIG. 6 in the direction indicated by the arrows.
Figure 8:
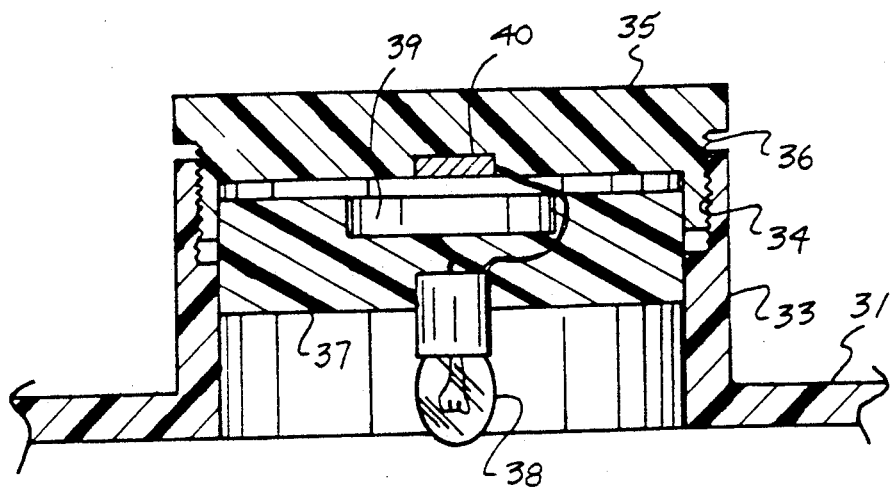
FIG. 8 is an enlarged orthographic view of the illumination bulb structure in association with the cap structure, as illustrated in FIG. 7.

FIG. 7 includes a cap member cylindrical side wall 30, with a cap top wall 31. A magnetic ring 32 is mounted within the cylindrical cap side wall 30 for magnetic adherence to the ferrous metallic ring 28 to permit securement of the cap member relative to the photo-cell cylindrical housing 26. A top wall cylindrical tube 33 includes a tube internally threaded portion 34 to threadedly receive a tube lid 35 having a tube lid externally threaded skirt 36. A mounting web 37 is mounted within the cylindrical tube 33 mounting an illumination bulb 38. A bulb battery 39 is mounted into the mounting web 37 in electrical communication with the illumination bulb, wherein the illumination bulb is in electrical communication with an electrical contact plate 40, whereupon threaded projection of the tube lid 35 effects communication of the contact plate 40 with the bulb battery 39, wherein a first electrical wire is directed from the illumination bulb 38 to the contact plate 40, with the second electrical wire directed from the illumination bulb 38 to the bulb battery 39, whereupon communication of the contact plate 40 with the bulb battery 39 effects completion of a circuitry to effect illumination of the illumination bulb 38 to thereby direct illumination of the photo-cell plate 27 and maintain the sunglass set in the second position, as indicated in FIG. 1.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A sunglass raising and lowering apparatus, comprising in combination, a sun visor, the sun visor having a visor concave bottom surface coextensive with a visor convex top surface, and a continuous annular band mounted to the visor for securement about an individual's head portion, and a battery member arranged for securement relative to the band, and a solenoid in electrical communication with the battery mounted to the band, with the solenoid having a solenoid link extending through the visor, and a sunglass set mounted to the visor in adjacency to the visor concave bottom surface, said sunglass set including a sunglass frame leg, the sunglass frame leg including a cam plate fixedly and orthogonally mounted to the frame leg, with the solenoid link secured to the cam plate to effect rotation of the cam plate and the sunglass set from a first position in adjacency to the visor concave bottom surface to a second position displaced relative to the visor concave bottom surface.

2. An apparatus as set forth in claim 1 including an axle shaft having a plurality of support blocks, wherein the support blocks are fixedly mounted to the visor concave bottom surface, and the axle shaft rotatably mounts the cam plate about the axle shaft, with the axle shaft arranged parallel relative to the frame leg.

3. An apparatus as set forth in claim 2 including a photo-cell switch mounted to the band in electrical communication with the solenoid and the battery to effect actuation of the solenoid upon the photo-cell switch sensing available sunlight.

4. An apparatus as set forth in claim 3 wherein the photo-cell switch includes a photo-cell cylindrical housing, the photo-cell cylindrical housing including a ferrous metallic ring mounted in surrounding relationship relative to the photo-cell cylindrical housing, with a cap member, the cap member including a cap member cylindrical side wall, the cap member cylindrical side wall including a magnetic ring mounted within the cap member cylindrical side wall for magnetic adherence to the ferrous metallic ring to secure the cap member to the photo-cell cylindrical housing, and the cap member including a cap top wall, the cap top wall including a top wall cylindrical tube, the tube having a tube internally threaded portion and a tube lid, the tube lid including an externally threaded skirt arranged for securement within the tube internally threaded portion to direct the tube skirt into the tube, and a mounting web mounted within the cylindrical tube, the mounting web including an illumination bulb, and a bulb battery mounted within the mounting web, and an electrical contact plate mounted within the tube lid, with the contact plate in electrical communication with the illumination bulb, and the battery arranged in electrical communication with the illumination bulb, whereupon projecting the externally threaded skirt into the tube effects communication between the electrical contact plate and the bulb battery to effect illumination of the illumination bulb and direct illumination onto the photo-cell switch to pivot the sunglass set to the second position.

* * * * *